United States Patent [19]

Söder et al.

[11] 4,091,095
[45] May 23, 1978

[54] PHOSPHINYL COMPOUNDS

[75] Inventors: Alfons Söder, Frankfurt-Schwanheim; Klaus Perrey, Bonn-Bad Godesberg, both of Germany

[73] Assignee: Hoechst Aktiengesellschaft, Germany

[21] Appl. No.: 702,604

[22] Filed: Jul. 6, 1976

[51] Int. Cl.² .................... A61K 31/66; C07C 101/50
[52] U.S. Cl. ................................ 424/211; 260/283 P; 260/287 AR; 260/295 P; 424/258; 424/266; 560/48
[58] Field of Search ..................... 260/471 R; 424/211

[56] References Cited

U.S. PATENT DOCUMENTS

| | | | |
|---|---|---|---|
| 3,644,368 | 2/1972 | Allais | 260/287 R |
| 3,692,818 | 7/1970 | Boltze et al. | 260/471 R |
| 3,714,009 | 1/1973 | Kleiner | 204/162 HE |

OTHER PUBLICATIONS

Morrison & Boyd, "Organic Chemistry," Dec., 1973, p. 583.
Verlag, Georg Thieme, "Methoden der organischen Chemie," vol. XII/1, pp. 153–155, 1963.

*Primary Examiner*—Donald G. Daus
*Assistant Examiner*—Lisa Jones
*Attorney, Agent, or Firm*—Berman, Aisenberg & Platt

[57] ABSTRACT

A phosphinyl derivative of formula

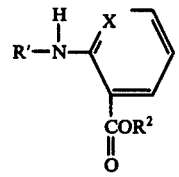

wherein
X is selected from the group consisting of a carbon atom with a hydrogen atom attached thereto and a nitrogen atom,
$R^1$ is
  a. a phenyl radical,
  b. a quinolyl radical,
  c. one of the radicals (a) and (b) being substituted by at least one substituent selected from the group consisting of halogen, trifluoromethyl and 1 to 3 alkyl radicals having in total up to 4 carbon atoms,
$R^2$ is selected from the group consisting of a dialkylphosphinylalkyl radical and a dialkyl phosphinylhydroxyalkyl radical each of said radicals $R^2$ having a total of from 3 to 7 carbon atoms and acid addition salts thereof, pharmaceutical preparations containing said derivatives.

9 Claims, No Drawings

PHOSPHINYL COMPOUNDS

This invention relates to certain new phosphinyl derivatives having interesting physiological activities.

Certain aminocarboxylic acid esters, for example 2,3-dihydroxypropyl N-(7-chloro-4-quinolyl)-anthranilate (which is insoluble in water), are known to have analgesic activity but difficulties have arisen in using them in pharmaceutical preparations owing to their limited solubility.

According to one aspect of the present invention we provide compounds of general formula

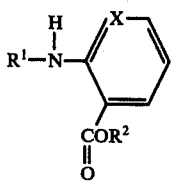

(wherein X represents CH or N; $R^1$ represents a phenyl or quinolyl group or such a group substituted by a halogen atom, a trifluoromethyl group or by from 1 to 3 alkyl groups having a total of up to 4 carbon atoms; and $R^2$ represents a dialkylphosphinylalkyl group containing a total of from 3 to 7 carbon atoms and each alkyl group being optionally substituted by a hydroxyl group) and acid addition salts thereof.

The compounds according to the invention in general have valuable physiological properties, in particular an analgesic, anti-inflammatory and anti-rheumatic activity with no undesirable side effects. Moreover they have a favourable degree of solubility in water and are stable, generally crystalline and compatible, compounds.

Preferred compounds include those wherein the dialkylphosphinylalkyl group $R^2$ has from 1 to 4 carbon atoms in each alkyl group or more especially wherein $R^2$ is a dimethylphosphinylalkyl group.

The compounds of general formula I may be prepared by any of the following processes, which processes constitute further aspects of the present invention:

a. Reaction of a carboxylic acid of formula

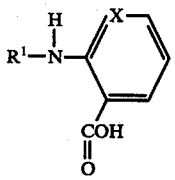

(wherein X and $R^1$ are as hereinbefore defined) or a reactive derivative thereof with an alcohol of formula

(wherein $R^2$ is as hereinbefore defined);

b. Reaction of a salt of a carboxylic acid of formula II above with an alkyl halide of formula

(wherein $R^2$ is as hereinbefore defined and Hal represents a halogen atom);

c. For the preparation of a compound of formula I wherein $R^1$ represents a quinolyl group optionally substituted as aforesaid:
Reaction of a compound of formula

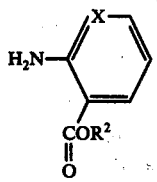

(wherein $R^2$ is as hereinbefore defined and which the alkylene radical thereof has 1 to 5, preferably 1 to 3 carbon atoms) with 4-chloroquinoline or with a 4-chloroquinoline substituted by a further halogen atom, a trifluoromethyl group or by from 1 to 3 alkyl groups having a total of up to 4 carbon atoms;

d. Reaction of an ester of formula

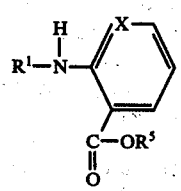

[wherein $R^1$ and X are as hereinbefore defined and $R^5$ represents an alkenyl or oxoalkyl group having 2 to 6 carbon atoms (for the preparation of a compound of formula I wherein $R^2$ contains the group:

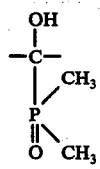

containing from 2 to 6 carbon atoms] with dimethylphosphine oxide of formula

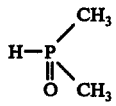

e. For the preparation of a compound of formula I wherein $R^2$ represents a dimethylphosphinylhydroxyalkyl group: Reaction of an appropriate epoxyalkyl ester of formula

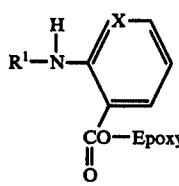

(wherein $R^1$ and X are as hereinbefore defined) with a compound of formula

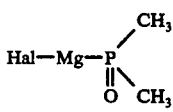
(XII)

(wherein Hal is as hereinbefore defined)

The reaction according to method (b) proceeds particularly smoothly. Reaction (c) will generally be preferred for the preparation of a phosphinyl derivative of a carboxylic acid of formula II which is not very soluble in organic solvents from an ester starting material which is relatively readily soluble in organic solvents. According to reaction (d), phosphinyl derivatives wherein the alkylene group in the $R^2$ group between the ester group and the $>P=O$ group carries an OH group may be prepared from the oxoalkyl esters of formula (VIII). By this means the solubility of the products can for example be increased. Reaction (e) may with advantage be used when it is desired to introduce an OH group into a side-chain of the alkylene group in the group $R^2$. For the preparation of such compounds method (e) is generally preferred to method (b) using an alkyl halide of formula IV.

Generally, reactions (a) to (e) are carried out at a temperature of up to 200° C, preferably at 20° to 180° C. It is also possible to work in the presence of a gas which is inert under the reaction conditions, e.g. nitrogen.

Conveniently, reaction (a) is carried out in the presence of a dehydration agent, for example an acid catalyst, e.g. hydrochloric acid, hydrobromic acid, sulphuric acid or toluenesulphonic acid or a cation exchanger in the hydrogen form, or a carbodiimide, for example dicyclohexylcarbodiimide, 1-cyclohexyl-3-(2-morpholinomethyl)-carbodiimide, 1-(3-dimethylaminopropyl)-3-ethyl-carbodiimide hydrochloride, di-p-tolyl-carbodiimide and diisopropylcarbodiimide, and N,N'-carbonyldiimidazole. If necessary, the water formed on esterification is removed by distillation with an entrainer, for example benzene or toluene, as an azeotropic mixture. However, it is also possible to work in the absence of a catalyst.

Reaction (a) is preferably carried out using a molar ratio of carboxylic acid to alcohol of from 1:1 to 1.5:1 and effecting the reaction in an inert solvent and in the presence of dicyclohexylcarbodiimide. The temperatures may vary depending on the solvent or dehydration catalyst chosen. Thus, in the presence of the above mentioned carbodiimide, and of benzene or toluene, it is particularly advantageous to work at temperatures of from 70° to 110° C, whereas reactions in the presence of carbonyldiimidazole are generally carried out at lower temperatures, advantageously at from 20° to 60° C.

Alcohols of general formula III which may be used in method (a) are, for example, the following:

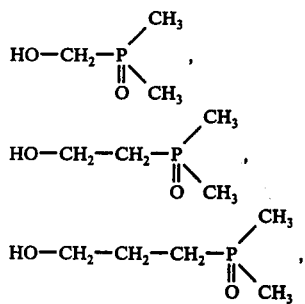

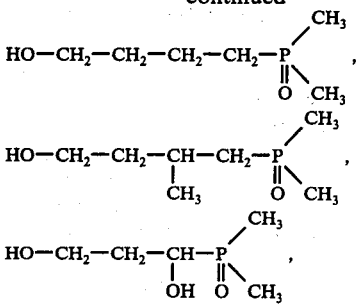

i.e., phosphinyl alcohols which have 1 to 4 carbon atoms in the main chain between the alcoholic OH group and the phosphinyl group.

The carboxylic acids of general formula II which are used are N-$R^1$-substituted anthranilic and β-nicotinic acids.

Suitable reactive derivatives of acids of general formula II which may be used in method a) include, for example, the anhydrides, halides of formula

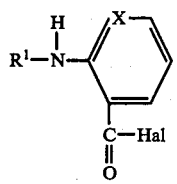
(V)

and alkyl esters with 1 to 6 carbon atoms, preferably 1 to 3 carbon atoms, in the alkyl group, of formula

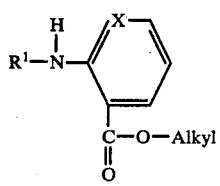
(VI)

The reaction of acid derivatives is also conveniently carried out in the presence of catalysts or adjuvants. Thus, carboxylic acid halides are preferably reacted in the presence of alkali metal carbonates or tertiary amines, e.g. pyridine or picoline, and generally in an inert solvent, such as benzene or toluene. Temperatures of from 15° to 90° C, preferably 20° to 40° C, may be used.

Cyclic anhydrides of general formula

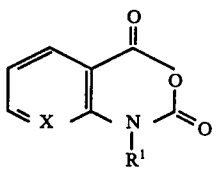
(VII)

may also be used as starting materials for method (a). The desired ester is advantageously formed in the presence of a catalytic quantity of an alkali metal hydroxide, e.g. sodium hydroxide or potassium hydroxide, with the release of carbon dioxide at temperatures of from 65° to 100° C.

The alkyl group of the carboxylic acid esters according to formula VI used as starting materials conveniently has not more than three carbon atoms, so that the alcohols liberated in the interchange of ester radicals can easily be removed from the reaction mixture. The ester interchange is conveniently catalysed by means of acids or bases, e.g. mineral acids, ion exchangers, sodium and potassium metal, sodium hydride and sodium amide.

For reaction (b), alkali metal, alkaline earth metal and tertiary ammonium salts of compounds of general formula II are preferably used, for example ammonium salts derived from the following tertiary amines: ethyl-bis-(isopropyl)-amine, ethyl-bis-(cyclohexyl)-amine, tris-[2-hydroxypropyl-(1-)]-amine and 1,8-bis-(dimethylamino)-naphthalene. The halides of formula IV used correspond to the alcohols of formula III used for reaction (a), except that instead of the hydroxyl group in the end position, there is a halogen atom, e.g. chlorine or bromine. A typical halide of formula IV is the compound

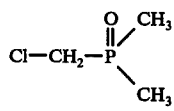

Reaction (c) proceeds in such a way that the N atom is directly linked to the quinolyl group. For this reaction, the presence of a catalyst, e.g. a mineral acid, is again preferred. Suitable quinoline compounds include the following:

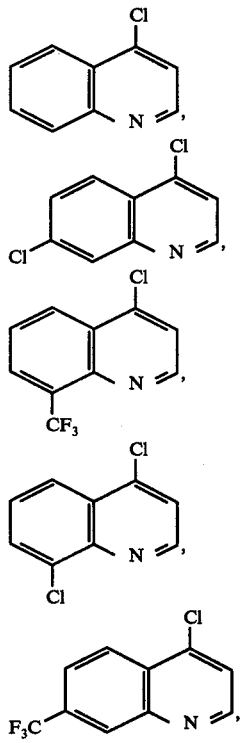

Reactions (d) are preferably effected at temperatures of from 40° to 180° C. Reactions involving the addition of the dimethylphosphinyl oxide to an olefinic double bond of an alkenyl compound are advantageously effected in the presence of a radical forming agent and/or under UV light, and those involving the addition of the dimethylphosphine oxide to an oxo group may be effected in the presence of bases. Suitable radical forming agents are e.g. α,α-azo-bis-isobutyronitrile, azo-bis-isobutanol diacetate, phenylazotriphenylmethane, tetraphenylsuccinic acid dinitrile and di-tertbutyl peroxide. Suitable bases are e.g. quinuclidine, 3-hydroxyquinuclidine, triethylenediamine and pentamethyl guanidine.

Typical alkenyl esters according to general formula VIII which may be used for process (d) are those of formula

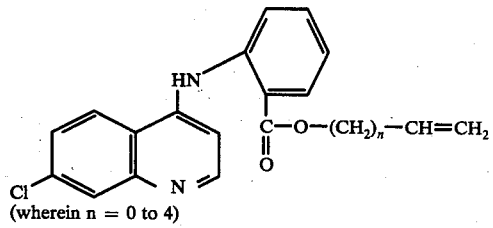

(wherein n = 0 to 4)

the allyl ester being especially preferred. If an oxoalkyl ester of formula VIII is used as reaction component, the oxo group is preferably separated from the ester group by at least one carbon atom.

Reaction (e) is preferably effected in the presence of a solvent, for example tetrahydrofuran or dioxan, and at a temperature of from 50° to 120° C. Work up involves subsequent hydrolysis for example with an alkali, e.g. aqueous potassium carbonate. Typical is the reaction of 2,3-epoxypropyl-N-(7-chloro-4-quinolyl)-anthranilate (melting point 150° to 152° C) and dimethylphosphinyl magnesium chloride.

The compounds of general formula I according to the invention may be formulated into pharmaceutical compositions suitably adapted for oral, parenteral or rectal administration. Thus according to a further feature of the invention we provide pharmaceutical compositions comprising as active ingredient at least one compound of formula I according to the invention in association with a solid or liquid pharmaceutical carrier or excipient.

Such compositions are desirably presented in the form of dosage units, each dosage unit being adapted to supply a fixed dose of active ingredient.

If desired one or more further pharmaceutically active ingredients, e.g. pyrazolones or xanthines, may be formulated into the composition.

The compounds may be formulated into all conventional forms of administration, for example, solutions, suspensions, powders, tablets, coated tablets, suppositories, granulates and delayed release forms. Processing of the compositions is carried out in the usual way using the excipients conventionally used for the purpose, for example carriers, disintegrants, binders, coating agents, swelling agents, lubricants, flavourings, sweeteners, means for obtaining delayed release and solvating agents. Suitable excipients thus include, for example, lactose, mannitol, talc, stearic acid and its salts, chlorides, phosphates, carbonates, milk protein, starch, gelatine, cellulose and derivatives thereof, e.g. methyl cellulose and hydroxyethyl cellulose and suitable swelling and non-swelling copolymers. Extenders may be used in small or large quantities to control the decomposition of the composition and thus the release of the active substances.

The following Examples serve to illustrate the preparation of compounds of general formula I according to the invention:

EXAMPLE 1 a) 6.1 grams (0.02 mol) of sodium N-(3-trifluoromethyl-phenyl)-anthranilate and 3.2 grams (0.025 mol) of chloromethyl-dimethyl-phosphine oxide are heated together with stirring, at 150° C in 100 ml of dimethylformamide, under a nitrogen atmosphere. After the sodium chloride and solvent have been separated off, the ester is taken up in methanol. A small amount of impurity present may be removed, using neutral aluminium oxide, by column chromatography or by recrystallisation, e.g. from ether.

The product is purified by thin layer chromatography using prefabricated $F_{254}$ silica gel plates made by the firm Merck. Eluant: chloroform-methanol-30% aqueous ammonia solution (volume ratio 85:14:1). Detection: UV light.

6.8 grams (92% of theory) of dimethylphosphinyl-methyl N-(3-trifluoromethyl-phenyl)-anthranilate are obtained. Melting point: 85° C; $R_f$ value: 0.85.

b. The same compound is obtained by reacting N-(3-trifluoromethylphenyl)-anthranilic acid with hydroxymethyldimethylphosphine oxide at 110° C, using toluene as an entrainer to remove the reaction water and gaseous hydrogen chloride as catalyst.

(c) to (f) The following were prepared by methods analogous to the above:

c. Dimethylphosphinyl-methyl N-(2,3-dimethyl-phenyl)-anthranilate; melting point: 177° C; $R_f$ value. 0.80.

d. Dimethylphosphinyl-propyl N-(2,3-dimethylphenyl)-anthranilate; melting point 131° C.

e. Dimethylphosphinyl-propyl N-(3-trifluoromethyl-phenyl)-anthranilate; melting point: 102° C.

f. 3-(Dimethylphosphinyl)-propyl N-(8-trifluoromethyl-4-quinolyl)-anthranilate; melting point 122° C.

EXAMPLE 2 a. Under an inert gas (nitrogen) and with stirring, a mixture of 7.1 grams (0.02 mol) of sodium N-(8-trifluoromethyl-4-quinolyl)-anthranilate, 3.8 grams (0.03 mol) of chloromethyldimethylphosphine oxide and 100 ml of dimethylformamide is heated at 120° C for 15 hours. The crystalline sodium chloride produced is removed and dimethylphosphinylmethyl N-(8-trifluoromethyl-4-quinolyl)-anthranilate is isolated after concentrating the reaction solution. The crystals obtained can be recrystallized from ether. Melting point: 176° C, Yield: 8.0 grams (95% of theory). (b) to (e) The following esters b. 3-(dimethylphosphinyl)-propyl N-(7-chloro-4-quinolyl)-anthranilate (melting point 165° C), c. 3-(dimethylphosphinyl)-methyl N-(7-chloro-4-quinolyl)-anthranilate (melting point 164° C), d. 3-(dimethylphosphinyl)-methyl 2-(3-trifluoromethylanilino)-nicotinate (melting point 124° C) and e. 3-(dimethylphosphinyl)-propyl 2-(3-trifluoromethylaniline)-nicotinate (melting point 165° C) were obtained analogously.

EXAMPLE 3

4.6 grams (0.02 mol) of dimethylphosphinylmethyl anthranilate and 4.6 grams (0.02 mol) of 4-chloro-8-trifluoromethylquinoline are kept at 80° C for about 3½ hours in 15 ml of isopropanol and 2.3 ml of concentrated aqueous hydrochloric acid. After removing the solvents and excess hydrochloric acid, the free base of the ester is liberated at 0° C. The dimethylphosphinyl-methyl N-(8-trifluoromethyl-4-quinolyl)-anthranilate obtained is identical to that prepared in Example (2a). Yield 7.6 grams (90% of theory).

EXAMPLE 4

A mixture of 3.37 grams (0.01 mol) of allyl 7-chloro-4-quinolyl-anthranilate (melting point 112° C) dissolved in 60 ml of toluene and 1.17 grams (0.015 mol) of dimethylphosphine oxide is heated to 100° C. 30 mg of $\alpha,\alpha'$-azo-bis-isobutyronitrile in 10 ml of toluene are then added dropwise to catalyse the addition of the dimethylphosphine oxide to the allyl double bond. From the cooled solution, 3-(dimethylphosphinyl)-propyl N-(7-chloro-4-quinolyl)-anthranilate is isolated; melting point 162° C (after recrystallisation from acetone); yield: 3.58 grams (86% of theory).

The physiological activity of the compounds prepared in the Examples has been tested using various test methods and compared with the activities of various structurally similar commercial products. In each case, testing was carried out with equimolar quantities of the test compounds.

The toxicity was measured by oral administration to 50 mice.

The analgesic activity was determined by the Writhing Test in the mouse using the method of E. Siegmund et al (Proceed. Soc. - Exp. Biol. Med. 95 (1957) Page 729) and by the Randall-Selitto Test in the rat using the method of Randall and Selitto (Arch. Int. Pharmacodyn. 111 (1957) Page 409).

The anti-inflammatory effect was measured by the carrageenin oedema test on rat paws using the method of Winter et al (Proceed. Soc. Exp. Biol. Med. 111 (1962) Page 544) and in test series III) and also by the adjuvant arthritis test in the rat according to Pearson et al (Arthrit. Rheumat. 2 (1959) page 440).

The test results are assembled in the following Table.

The following comparison compounds were used in the tests

| Substance | Name |
| --- | --- |
| A | Glafenin |
| B | Mefenamic acid |
| C | Flufenamic acid |
| D | Nifluminic acid | and the compounds of Examples (1a), (1c) to (1f), (2a), (2c) to (2e) and 4, according to the invention.

Table

| Compound under test | Toxicity ED 50 | Writhing Test | Randall-Selitto Test | Carrageenin oedema | Adjuvant arthritis |
| --- | --- | --- | --- | --- | --- |
| Test Series I | | | | | |
| A (Comp) | 2020 | 25.9 | 99.2 | 14.3 | — |
| 2c (Invent.) | 596 | 20.4 | 133 | 8.3 | — |
| 2a (Invent.) | >2800 | 5.58 | 91.5 | 16.8 | — |
| 4 (Invent.) | 770 | 26.0 | 110 | 11.5 | — |
| Test Series II | | | | | |
| B (Comp) | 2500 | 36.3 | 53.6 | 20.5 | — |
| 1c (Invent) | >3000 | 37.8 | 32.1 | 19.2 | — |
| 1d (Invent) | 2725 | 21.7 | >200 | 25.5 | — |
| Test Series III | | | | | |
| C (Comp) | 1200 | 34.3 | 40.8 | 6.04 | 25-50 |

Table-continued

| Compound under test | Toxicity ED 50 | Writhing Test | Randall-Selitto Test | Carrageenin oedema | Adjuvant arthritis |
|---|---|---|---|---|---|
| 1a (Invent) | >2000 | 19.5 | 30.8 | 6.92 | 5-10 |
| 1e (Invent) | 2650 | >100 | 36.1 | 5.46 | 10-25 |
| 1f (Invent) | — | 12.3 | 225 | 15.5 | — |
| Test Series IV | | | | | |
| D (Comp) | 945 | 21.5 | 37.0 | 9.1 | — |
| 2d (Invent) | >2000 | 10.9 | 29.0 | 8.6 | — |
| 2e (Invent) | — | 30.0 | >200 | 20.9 | — |

DISCUSSION OF THE RESULTS

As the above Table shows, in Test Series I the toxicity of Compound (2a) only is lower than that of Compound A. However the activity spectrum of the compounds tested according to the invention is generally better overall. Thus, it is apparent that in the Writhing test, Compounds 2c and especially 2a are substantially better than the Comparison compound and the same is true of Compound 2a in the Randall-Selitto test. In the Carrageenin oedema test on the rat paw, compounds 2c and 4 show an improvement compared with compound A.

In test Series II, Compounds 1c and 1d have a more favourable toxicity than Compound B. The analgesic activity of Compound 1d in the Writhing test and that of Compound 1c in the Randall-Selitto test shows a substantial improvement over the Comparison Compound. The anti-inflammatory activities of Compounds 1c and 1d are more or less equivalent to those of the commercial compound.

In Test Series III, the anti-inflammatory properties of Compounds 1a and 1e in the sub-chronic adjuvant arthritis test are considerably better than that of Comparison Compound C. The analgesic activities of Compounds 1a and 1f are clearly improved over that of Comparison Compound C. The toxicities of Compounds 1a and 1e are substantially more favourable than that of Compound C.

The toxicity test on Compound 2d in Test Series IV gives a value more than twice that of Comparison Compound D and is thus substantially more favourable. The analgesic activity of these compounds both in the Writhing Test and in the Randall-Selitto test is also substantially better than that of the Comparison Compound. The anti-inflammatory activity of Compound 2d in the Carrageenin oedema test is practically almost equal to that of the Comparison Compound.

It is not intended that the examples given herein should be construed to limit the invention thereto, but rather they are submitted to illustrate some of the specific embodiments of the invention. Resort may be had to various modifications and variations of the present invention without departing from the spirit of the discovery or the scope of the appended claims.

What we claim is:

1. A member selected from the group consisting of a) a compound of the formula

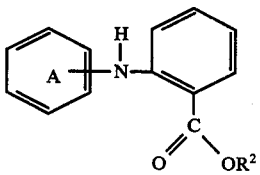

wherein
$R^2$ has a total of from 3 to 7 carbon atoms and is a member selected from the group consisting of dialkylphosphinylalkyl and dialkylphosphinylhydroxyalkyl; and A designates a nucleus which is optionally substituted by at least one substituent selected from the group consisting of halogen, trifluoromethyl and from 1 to 3 alkyl radicals having a total of up to 4 carbon atoms;

and b) an acid-addition salt of (a).

2. A member as claimed in claim 1 wherein $R^2$ is dialkylphosphinylalkyl.

3. A member as claimed in claim 1 wherein $R^2$ is dimethylphosphinylmethyl.

4. A member as claimed in claim 1 wherein $R^2$ is dimethylphosphinylpropyl.

5. A member as claimed in claim 1 wherein $R^2$ is selected from the group dimethylphosphinalkyl and dimethylphosphinyl-hydroxyalkyl.

6. A member as claimed in claim 1 which is a dialkyl phosphinyl alkylester of N-(3-trifluoromethylphenyl)anthranilic acid or an acid-addition salt thereof.

7. A member as claimed in claim 1 wherein A designates unsubstituted phenyl.

8. A member as claimed in claim 1 wherein A designates a nucleus which is substituted by from one to three alkyl radicals having a total of up to four carbon atoms.

9. A pharmaceutical preparation having analgesic activity and containing an effective dose of a member as claimed in claim 1 in combination with at least one solid or fluid carrier or additive.

* * * * *

UNITED STATES PATENT AND TRADEMARK OFFICE
CERTIFICATE OF CORRECTION

PATENT NO. : 4,091,095
DATED : May 23, 1978
INVENTOR(S) : SÖDER ET AL

It is certified that error appears in the above-identified patent and that said Letters Patent are hereby corrected as shown below:

Title page, left column, third line under "OTHER PUBLICATIONS", "Verlag, Georg Thieme" should read --Houben-Weyl--; right column, in the formula, "R'" should read --$R^1$--. Column 10, line 37, "dimethylphosphinalkyl" should read --dimethylphosphinylalkyl--.

Signed and Sealed this

Twenty-seventh Day of February 1979

[SEAL]

Attest:

RUTH C. MASON
Attesting Officer

DONALD W. BANNER
Commissioner of Patents and Trademarks